(12) United States Patent
Stubbs et al.

(10) Patent No.: US 8,076,148 B2
(45) Date of Patent: Dec. 13, 2011

(54) CYTOCHROME C PROTEIN AND ASSAY

(75) Inventors: Simon L. Stubbs, Cardiff (GB);
Michael J. Francis, Cardiff (GB);
Adrian Cushing, Cardiff (GB);
Rahman A. Ismail, Cardiff (GB)

(73) Assignee: GE Healthcare UK Limited, Little Chalfont (GB)

( * ) Notice: Subject to any disclaimer, the term of this patent is extended or adjusted under 35 U.S.C. 154(b) by 1221 days.

(21) Appl. No.: 10/583,591

(22) PCT Filed: Dec. 17, 2004

(86) PCT No.: PCT/GB2004/005317
§ 371 (c)(1),
(2), (4) Date: Jun. 19, 2006

(87) PCT Pub. No.: WO2005/058960
PCT Pub. Date: Jun. 30, 2005

(65) Prior Publication Data
US 2009/0053748 A1    Feb. 26, 2009

(30) Foreign Application Priority Data

Dec. 19, 2003   (GB) ................................. 0329353.7

(51) Int. Cl.
| | | |
|---|---|---|
| G01N 33/00 | (2006.01) | |
| C12N 15/00 | (2006.01) | |
| C12N 1/20 | (2006.01) | |
| C07K 1/00 | (2006.01) | |

(52) U.S. Cl. ..................... 436/86; 435/252.3; 435/320.1; 530/350; 536/23.1

(58) Field of Classification Search ..................... 436/86; 536/23.1; 435/252.3, 320.1; 530/350
See application file for complete search history.

(56) References Cited

U.S. PATENT DOCUMENTS

| | | | |
|---|---|---|---|
| 5,932,474 A | 8/1999 | Tsien et al. | |
| 6,008,378 A | 12/1999 | Tsien et al. | |
| 6,054,271 A | 4/2000 | Tsien et al. | |
| 6,172,188 B1 | 1/2001 | Thastrup et al. | |
| 6,270,964 B1 | 8/2001 | Michnick et al. | |
| 6,294,330 B1 | 9/2001 | Michnick et al. | |
| 6,428,951 B1 | 8/2002 | Michnick et al. | |
| 2003/0175859 A1 | 9/2003 | Stubbs et al. | |

FOREIGN PATENT DOCUMENTS

| | | |
|---|---|---|
| EP | 1 354 953 | 10/2003 |
| GB | 2 374 868 | 10/2002 |
| WO | WO 02/085936 | 10/2002 |
| WO | WO 02/08752 | 1/2003 |

OTHER PUBLICATIONS

Evans et al., Uniprot database, accession No. p9999, 1986.*
Abdullaev, Z., et al., "A Cytochrome c Mutant with High Electron Transfer and Antioxidant Activities but Devoid of Apoptogenic Effect", *Biochemical Society Journal*, vol. 362, 2002, p. 749-754.
Chandra, D., et al., "Early Mitochondrial Activation and Cytochrome C Up-Regulation During Apoptosis", *Journal of Biological Chemistry*, vol. 277, 2002, p. 50842-50854.
Lim, M., et al., "On the Release of Cytochrome D from Mitochondria during Cell Death Signaling", *J Biomed Sci*, vol. 9, 2002, p. 488-506.
Gao, W., et al., "Temporal Relationship between Cytochrome c Release and Mitochondrial Swelling during UV-induced Apoptosis in Living HeLa Cells", *Journal of Cell Science*, vol. 114, 2001, p. 2855-2862.
Goldstein, J., et al., "The Coordinate Release of Cytochrome c during Apoptosis Rapid, Complete and Kinetically Invariant", *Nature Cell Biology*, vol. 2, 2000, p. 156-162.
Yu, T., et al., "A Mutational Epitope for Cytochrome c Binding to the Apoptosis Protease Activation Factor-1", *The Journal of Biological Chemistry*, vol. 276, 2001, p. 13034-13038.
Kluck, R., et al., Journal of Biological Chemistry, (2000), 275(21), 16127-16133.
Li, P., et al., Cell, (1997), 91, 479-489.

* cited by examiner

Primary Examiner — Maryam Monshipouri

(57) ABSTRACT

The present invention relates to a cytochrome c-reporter fusion protein construct comprising a modified cytochrome c protein which targets the mitochondria and has a reduced ability to induce apoptosis in a living cell. The invention also relates to nucleic acid constructs encoding such protein fusions and cells stably transfected with such constructs. The stably transfected cells of the invention can be used in assays to detect apoptosis.

29 Claims, 18 Drawing Sheets
(3 of 18 Drawing Sheet(s) Filed in Color)

Figure 4. SEQ ID NO: 1 - Wild Type Cytochrome C (NM_018947)

```
      Met Gly Asp Val Glu Lys Gly Lys Lys Ile Phe Ile Met Lys Cys Ser
  1   ATG GGT GAT GTT GAG AAA GGC AAG AAG ATT TTT ATT ATG AAG TGT TCC

Gln Cys His Thr Val Glu Lys Gly Gly Lys His Lys Thr Gly Pro Asn
 49   CAG TGC CAC ACC GTT GAA AAG GGA GGC AAG CAC AAG ACT GGG CCA AAT

Leu His Gly Leu Phe Gly Arg Lys Thr Gly Gln Ala Pro Gly Tyr Ser
 97   CTC CAT GGT CTC TTT GGG CGG AAG ACA GGT CAG GCC CCT GGA TAC TCT

Tyr Thr Ala Ala Asn Lys Asn Lys Gly Ile Ile Trp Gly Glu Asp Thr
145   TAC ACA GCC GCC AAT AAG AAC AAA GGC ATC ATC TGG GGA GAG GAT ACA

Leu Met Glu Tyr Leu Glu Asn Pro Lys Lys Tyr Ile Pro Gly Thr Lys
193   CTG ATG GAG TAT TTG GAG AAT CCC AAG AAG TAC ATC CCT GGA ACA AAA

Met Ile Phe Val Gly Ile Lys Lys Lys Glu Glu Arg Ala Asp Leu Ile
241   ATG ATC TTT GTC GGC ATT AAG AAG AAG GAA GAA AGG GCA GAC TTA ATA

Ala Tyr Leu Lys Lys Ala Thr Asn Glu
289   GCT TAT CTC AAA AAA GCT ACT AAT GAG
```

Figure 5. SEQ ID NO: 2 - Wild Type Cytochrome C (NM_018947)

```
1
Met Gly Asp Val Glu Lys Gly Lys Lys Ile Phe Ile Met Lys Cys Ser
17
Gln Cys His Thr Val Glu Lys Gly Gly Lys His Lys Thr Gly Pro Asn
33
Leu His Gly Leu Phe Gly Arg Lys Thr Gly Gln Ala Pro Gly Tyr Ser
49
Tyr Thr Ala Ala Asn Lys Asn Lys Gly Ile Ile Trp Gly Glu Asp Thr
65
Leu Met Glu Tyr Leu Glu Asn Pro Lys Lys Tyr Ile Pro Gly Thr Lys
81
Met Ile Phe Val Gly Ile Lys Lys Lys Glu Glu Arg Ala Asp Leu Ile
97
Ala Tyr Leu Lys Lys Ala Thr Asn Glu
```

Figure 6. SEQ ID NO: 3    TriGFP-cytochrome C K72A

```
          Met Ser Lys Gly Glu Glu Leu Phe Thr Gly Val Val Pro Ile Leu Val
  1       ATG AGT AAA GGA GAA GAA CTT TTC ACT GGA GTT GTC CCA ATT CTT GTT

Glu Leu Asp Gly Asp Val Asn Gly His Lys Phe Ser Val Ser Gly Glu
 49       GAA TTA GAT GGT GAT GTT AAT GGG CAC AAA TTT TCT GTC AGT GGA GAG

Gly Glu Gly Asp Ala Thr Tyr Gly Lys Leu Thr Leu Lys Phe Ile Cys
 97       GGT GAA GGT GAT GCA ACA TAC GGA AAA CTT ACC CTT AAA TTT ATT TGC

Thr Thr Gly Lys Leu Pro Val Pro Trp Pro Thr Leu Val Thr Thr Leu
145       ACT ACT GGA AAA CTA CCT GTT CCA TGG CCA ACA CTT GTC ACT ACT CTC

Ser Tyr Gly Val Gln Cys Phe Ser Arg Tyr Pro Asp His Met Lys Arg
193       TCT TAT GGT GTT CAA TGC TTT TCA AGA TAC CCA GAT CAT ATG AAA CGG

His Asp Phe Phe Lys Ser Ala Met Pro Glu Gly Tyr Val Gln Glu Arg
241       CAT GAC TTT TTC AAG AGT GCC ATG CCC GAA GGT TAT GTA CAG GAA AGA

Thr Ile Phe Phe Lys Asp Asp Gly Asn Tyr Lys Thr Arg Ala Glu Val
289       ACT ATA TTT TTC AAA GAT GAC GGG AAC TAC AAG ACA CGT GCT GAA GTC

Lys Phe Glu Gly Asp Thr Leu Val Asn Arg Ile Glu Leu Lys Gly Ile
337       AAG TTT GAA GGT GAT ACC CTT GTT AAT AGA ATC GAG TTA AAA GGT ATT

Asp Phe Lys Glu Asp Gly Asn Ile Leu Gly His Lys Leu Glu Tyr Asn
385       GAT TTT AAA GAA GAT GGA AAC ATT CTT GGA CAC AAA TTG GAA TAC AAC

Tyr Asn Ser His Asn Val Tyr Ile Met Ala Asp Lys Gln Lys Asn Gly
433       TAT AAC TCA CAC AAT GTA TAC ATC ATG GCA GAC AAA CAA AAG AAT GGA

Ile Lys Val Asn Phe Lys Ile Arg His Asn Ile Glu Asp Gly Gly Val
481       ATC AAA GTT AAC TTC AAA ATT AGA CAC AAC ATT GAA GAT GGA GGC GTT

Gln Leu Ala Asp His Tyr Gln Gln Asn Thr Pro Ile Gly Asp Gly Pro
529       CAA CTA GCA GAC CAT TAT CAA CAA AAT ACT CCA ATT GGC GAT GGC CCT

Val Leu Leu Pro Asp Asn His Tyr Leu Ser Thr Gln Ser Ala Leu Ser
577       GTC CTT TTA CCA GAC AAC CAT TAC CTG TCC ACA CAA TCT GCC CTT TCG

Lys Asp Pro Asn Glu Lys Arg Asp His Met Val Leu Leu Gly Phe Val
625       AAA GAT CCC AAC GAA AAG AGA GAC CAC ATG GTC CTT CTT GGC TTT GTA

Thr Ala Ala Gly Ile Thr His Gly Met Asp Glu Leu Tyr Lys Leu Glu
673       ACA GCT GCT GGG ATT ACA CAT GGC ATG GAT GAA CTA TAC AAA CTC GAG

Asn Ser Thr Met Gly Asp Val Glu Lys Gly Lys Lys Ile Phe Ile Met
721       AAT TCG ACC ATG GGT GAT GTT GAG AAA GGC AAG AAG ATT TTT ATT ATG

Lys Cys Ser Gln Cys His Thr Val Glu Lys Gly Gly Lys His Lys Thr
769       AAG TGT TCC CAG TGC CAC ACC GTT GAA AAG GGA GGC AAG CAC AAG ACT

Gly Pro Asn Leu His Gly Leu Phe Gly Arg Lys Thr Gly Gln Ala Pro
817       GGG CCA AAT CTC CAT GGT CTC TTT GGG CGG AAG ACA GGT CAG GCC CCT

Gly Tyr Ser Tyr Thr Ala Ala Asn Lys Asn Lys Gly Ile Ile Trp Gly
```

Figure 6 (continued)

```
865   GGA TAC TCT TAC ACA GCC GCC AAT AAG AAC AAA GGC ATC ATC TGG GGA

Glu Asp Thr Leu Met Glu Tyr Leu Glu Asn Pro Ala Lys Tyr Ile Pro
913   GAG GAT ACA CTG ATG GAG TAT TTG GAG AAT CCC GCC AAG TAC ATC CCT

Gly Thr Lys Met Ile Phe Val Gly Ile Lys Lys Lys Glu Glu Arg Ala
961   GGA ACA AAA ATG ATC TTT GTC GGC ATT AAG AAG AAG GAA GAA AGG GCA

Asp Leu Ile Ala Tyr Leu Lys Lys Ala Thr Asn Glu
1009  GAC TTA ATA GCT TAT CTC AAA AAA GCT ACT AAT GAG
```

Figure 7: SEQ ID NO: 4 - triGFP-cytochrome C K72A

```
1
Met Ser Lys Gly Glu Glu Leu Phe Thr Gly Val Val Pro Ile Leu Val
17
Glu Leu Asp Gly Asp Val Asn Gly His Lys Phe Ser Val Ser Gly Glu
33
Gly Glu Gly Asp Ala Thr Tyr Gly Lys Leu Thr Leu Lys Phe Ile Cys
49
Thr Thr Gly Lys Leu Pro Val Pro Trp Pro Thr Leu Val Thr Thr Leu
65
Ser Tyr Gly Val Gln Cys Phe Ser Arg Tyr Pro Asp His Met Lys Arg
81
His Asp Phe Phe Lys Ser Ala Met Pro Glu Gly Tyr Val Gln Glu Arg
97
Thr Ile Phe Phe Lys Asp Asp Gly Asn Tyr Lys Thr Arg Ala Glu Val
113
Lys Phe Glu Gly Asp Thr Leu Val Asn Arg Ile Glu Leu Lys Gly Ile
129
Asp Phe Lys Glu Asp Gly Asn Ile Leu Gly His Lys Leu Glu Tyr Asn
145
Tyr Asn Ser His Asn Val Tyr Ile Met Ala Asp Lys Gln Lys Asn Gly
161
Ile Lys Val Asn Phe Lys Ile Arg His Asn Ile Glu Asp Gly Gly Val
177
Gln Leu Ala Asp His Tyr Gln Gln Asn Thr Pro Ile Gly Asp Gly Pro
193
Val Leu Leu Pro Asp Asn His Tyr Leu Ser Thr Gln Ser Ala Leu Ser
209
Lys Asp Pro Asn Glu Lys Arg Asp His Met Val Leu Leu Gly Phe Val
225
Thr Ala Ala Gly Ile Thr His Gly Met Asp Glu Leu Tyr Lys Leu Glu
241
Asn Ser Thr Met Gly Asp Val Glu Lys Gly Lys Lys Ile Phe Ile Met
257
Lys Cys Ser Gln Cys His Thr Val Glu Lys Gly Gly Lys His Lys Thr
273
Gly Pro Asn Leu His Gly Leu Phe Gly Arg Lys Thr Gly Gln Ala Pro
289
Gly Tyr Ser Tyr Thr Ala Ala Asn Lys Asn Lys Gly Ile Ile Trp Gly
305
Glu Asp Thr Leu Met Glu Tyr Leu Glu Asn Pro Ala Lys Tyr Ile Pro
321
Gly Thr Lys Met Ile Phe Val Gly Ile Lys Lys Lys Glu Glu Arg Ala
337
Asp Leu Ile Ala Tyr Leu Lys Lys Ala Thr Asn Glu
```

Figure 8. SEQ ID NO: 5 - Cytochrome C (K72A)-triGFP

```
         Met Gly Asp Val Glu Lys Gly Lys Lys Ile Phe Ile Met Lys Cys Ser
   1     ATG GGT GAT GTT GAG AAA GGC AAG AAG ATT TTT ATT ATG AAG TGT TCC

Gln Cys His Thr Val Glu Lys Gly Gly Lys His Lys Thr Gly Pro Asn
  49     CAG TGC CAC ACC GTT GAA AAG GGA GGC AAG CAC AAG ACT GGG CCA AAT

Leu His Gly Leu Phe Gly Arg Lys Thr Gly Gln Ala Pro Gly Tyr Ser
  97     CTC CAT GGT CTC TTT GGG CGG AAG ACA GGT CAG GCC CCT GGA TAC TCT

Tyr Thr Ala Ala Asn Lys Asn Lys Gly Ile Ile Trp Gly Glu Asp Thr
 145     TAC ACA GCC GCC AAT AAG AAC AAA GGC ATC ATC TGG GGA GAG GAT ACA

Leu Met Glu Tyr Leu Glu Asn Pro Ala Lys Tyr Ile Pro Gly Thr Lys
 193     CTG ATG GAG TAT TTG GAG AAT CCC GCC AAG TAC ATC CCT GGA ACA AAA

Met Ile Phe Val Gly Ile Lys Lys Lys Glu Glu Arg Ala Asp Leu Ile
 241     ATG ATC TTT GTC GGC ATT AAG AAG AAG GAA GAA AGG GCA GAC TTA ATA

Ala Tyr Leu Lys Lys Ala Thr Asn Glu Gly Arg Pro Gly Met Ser Lys
 289     GCT TAT CTC AAA AAA GCT ACT AAT GAG GGT CGA CCC GGG ATG AGT AAA

Gly Glu Glu Leu Phe Thr Gly Val Val Pro Ile Leu Val Glu Leu Asp
 337     GGA GAA GAA CTT TTC ACT GGA GTT GTC CCA ATT CTT GTT GAA TTA GAT

Gly Asp Val Asn Gly His Lys Phe Ser Val Ser Gly Glu Gly Glu Gly
 385     GGT GAT GTT AAT GGG CAC AAA TTT TCT GTC AGT GGA GAG GGT GAA GGT

Asp Ala Thr Tyr Gly Lys Leu Thr Leu Lys Phe Ile Cys Thr Thr Gly
 433     GAT GCA ACA TAC GGA AAA CTT ACC CTT AAA TTT ATT TGC ACT ACT GGA

Lys Leu Pro Val Pro Trp Pro Thr Leu Val Thr Thr Leu Ser Tyr Gly
 481     AAA CTA CCT GTT CCA TGG CCA ACA CTT GTC ACT ACT CTC TCT TAT GGT

Val Gln Cys Phe Ser Arg Tyr Pro Asp His Met Lys Arg His Asp Phe
 529     GTT CAA TGC TTT TCA AGA TAC CCA GAT CAT ATG AAA CGG CAT GAC TTT

Phe Lys Ser Ala Met Pro Glu Gly Tyr Val Gln Glu Arg Thr Ile Phe
 577     TTC AAG AGT GCC ATG CCC GAA GGT TAT GTA CAG GAA AGA ACT ATA TTT

Phe Lys Asp Asp Gly Asn Tyr Lys Thr Arg Ala Glu Val Lys Phe Glu
 625     TTC AAA GAT GAC GGG AAC TAC AAG ACA CGT GCT GAA GTC AAG TTT GAA

Gly Asp Thr Leu Val Asn Arg Ile Glu Leu Lys Gly Ile Asp Phe Lys
 673     GGT GAT ACC CTT GTT AAT AGA ATC GAG TTA AAA GGT ATT GAT TTT AAA

Glu Asp Gly Asn Ile Leu Gly His Lys Leu Glu Tyr Asn Tyr Asn Ser
 721     GAA GAT GGA AAC ATT CTT GGA CAC AAA TTG GAA TAC AAC TAT AAC TCA

His Asn Val Tyr Ile Met Ala Asp Lys Gln Lys Asn Gly Ile Lys Val
 769     CAC AAT GTA TAC ATC ATG GCA GAC AAA CAA AAG AAT GGA ATC AAA GTT

Asn Phe Lys Ile Arg His Asn Ile Glu Asp Gly Gly Val Gln Leu Ala
 817     AAC TTC AAA ATT AGA CAC AAC ATT GAA GAT GGA GGC GTT CAA CTA GCA

Asp His Tyr Gln Gln Asn Thr Pro Ile Gly Asp Gly Pro Val Leu Leu
```

Figure 8 (continued)

```
865 GAC CAT TAT CAA CAA AAT ACT CCA ATT GGC GAT GGC CCT GTC CTT TTA

Pro Asp Asn His Tyr Leu Ser Thr Gln Ser Ala Leu Ser Lys Asp Pro
913 CCA GAC AAC CAT TAC CTG TCC ACA CAA TCT GCC CTT TCG AAA GAT CCC

Asn Glu Lys Arg Asp His Met Val Leu Leu Gly Phe Val Thr Ala Ala
961 AAC GAA AAG AGA GAC CAC ATG GTC CTT CTT GGC TTT GTA ACA GCT GCT

Gly Ile Thr His Gly Met Asp Glu Leu Tyr Lys
1009 GGG ATT ACA CAT GGC ATG GAT GAA CTA TAC AAA
```

Figure 9. SEQ ID NO: 6 - Cytochrome C (K72A)-triGFP

```
1
Met Gly Asp Val Glu Lys Gly Lys Lys Ile Phe Ile Met Lys Cys Ser
17
Gln Cys His Thr Val Glu Lys Gly Gly Lys His Lys Thr Gly Pro Asn
33
Leu His Gly Leu Phe Gly Arg Lys Thr Gly Gln Ala Pro Gly Tyr Ser
49
Tyr Thr Ala Ala Asn Lys Asn Lys Gly Ile Ile Trp Gly Glu Asp Thr
65
Leu Met Glu Tyr Leu Glu Asn Pro Ala Lys Tyr Ile Pro Gly Thr Lys
81
Met Ile Phe Val Gly Ile Lys Lys Lys Glu Glu Arg Ala Asp Leu Ile
97
Ala Tyr Leu Lys Lys Ala Thr Asn Glu Gly Arg Pro Gly Met Ser Lys
113
Gly Glu Glu Leu Phe Thr Gly Val Val Pro Ile Leu Val Glu Leu Asp
129
Gly Asp Val Asn Gly His Lys Phe Ser Val Ser Gly Glu Gly Glu Gly
145
Asp Ala Thr Tyr Gly Lys Leu Thr Leu Lys Phe Ile Cys Thr Thr Gly
161
Lys Leu Pro Val Pro Trp Pro Thr Leu Val Thr Thr Leu Ser Tyr Gly
177
Val Gln Cys Phe Ser Arg Tyr Pro Asp His Met Lys Arg His Asp Phe
193
Phe Lys Ser Ala Met Pro Glu Gly Tyr Val Gln Glu Arg Thr Ile Phe
209
Phe Lys Asp Asp Gly Asn Tyr Lys Thr Arg Ala Glu Val Lys Phe Glu
225
Gly Asp Thr Leu Val Asn Arg Ile Glu Leu Lys Gly Ile Asp Phe Lys
241
Glu Asp Gly Asn Ile Leu Gly His Lys Leu Glu Tyr Asn Tyr Asn Ser
257
His Asn Val Tyr Ile Met Ala Asp Lys Gln Lys Asn Gly Ile Lys Val
273
Asn Phe Lys Ile Arg His Asn Ile Glu Asp Gly Gly Val Gln Leu Ala
289
Asp His Tyr Gln Gln Asn Thr Pro Ile Gly Asp Gly Pro Val Leu Leu
305
Pro Asp Asn His Tyr Leu Ser Thr Gln Ser Ala Leu Ser Lys Asp Pro
321
Asn Glu Lys Arg Asp His Met Val Leu Leu Gly Phe Val Thr Ala Ala
337
Gly Ile Thr His Gly Met Asp Glu Leu Tyr Lys
```

Figure 10. SEQ ID NO: 7 - TriGFP- wild type cytochrome C

```
      Met Ser Lys Gly Glu Glu Leu Phe Thr Gly Val Val Pro Ile Leu Val
  1   ATG AGT AAA GGA GAA GAA CTT TTC ACT GGA GTT GTC CCA ATT CTT GTT

Glu Leu Asp Gly Asp Val Asn Gly His Lys Phe Ser Val Ser Gly Glu
 49   GAA TTA GAT GGT GAT GTT AAT GGG CAC AAA TTT TCT GTC AGT GGA GAG

Gly Glu Gly Asp Ala Thr Tyr Gly Lys Leu Thr Leu Lys Phe Ile Cys
 97   GGT GAA GGT GAT GCA ACA TAC GGA AAA CTT ACC CTT AAA TTT ATT TGC

Thr Thr Gly Lys Leu Pro Val Pro Trp Pro Thr Leu Val Thr Thr Leu
145   ACT ACT GGA AAA CTA CCT GTT CCA TGG CCA ACA CTT GTC ACT ACT CTC

Ser Tyr Gly Val Gln Cys Phe Ser Arg Tyr Pro Asp His Met Lys Arg
193   TCT TAT GGT GTT CAA TGC TTT TCA AGA TAC CCA GAT CAT ATG AAA CGG

His Asp Phe Phe Lys Ser Ala Met Pro Glu Gly Tyr Val Gln Glu Arg
241   CAT GAC TTT TTC AAG AGT GCC ATG CCC GAA GGT TAT GTA CAG GAA AGA

Thr Ile Phe Phe Lys Asp Asp Gly Asn Tyr Lys Thr Arg Ala Glu Val
289   ACT ATA TTT TTC AAA GAT GAC GGG AAC TAC AAG ACA CGT GCT GAA GTC

Lys Phe Glu Gly Asp Thr Leu Val Asn Arg Ile Glu Leu Lys Gly Ile
337   AAG TTT GAA GGT GAT ACC CTT GTT AAT AGA ATC GAG TTA AAA GGT ATT

Asp Phe Lys Glu Asp Gly Asn Ile Leu Gly His Lys Leu Glu Tyr Asn
385   GAT TTT AAA GAA GAT GGA AAC ATT CTT GGA CAC AAA TTG GAA TAC AAC

Tyr Asn Ser His Asn Val Tyr Ile Met Ala Asp Lys Gln Lys Asn Gly
433   TAT AAC TCA CAC AAT GTA TAC ATC ATG GCA GAC AAA CAA AAG AAT GGA

Ile Lys Val Asn Phe Lys Ile Arg His Asn Ile Glu Asp Gly Gly Val
481   ATC AAA GTT AAC TTC AAA ATT AGA CAC AAC ATT GAA GAT GGA GGC GTT

Gln Leu Ala Asp His Tyr Gln Gln Asn Thr Pro Ile Gly Asp Gly Pro
529   CAA CTA GCA GAC CAT TAT CAA CAA AAT ACT CCA ATT GGC GAT GGC CCT

Val Leu Leu Pro Asp Asn His Tyr Leu Ser Thr Gln Ser Ala Leu Ser
577   GTC CTT TTA CCA GAC AAC CAT TAC CTG TCC ACA CAA TCT GCC CTT TCG

Lys Asp Pro Asn Glu Lys Arg Asp His Met Val Leu Leu Gly Phe Val
625   AAA GAT CCC AAC GAA AAG AGA GAC CAC ATG GTC CTT CTT GGC TTT GTA

Thr Ala Ala Gly Ile Thr His Gly Met Asp Glu Leu Tyr Lys Leu Glu
673   ACA GCT GCT GGG ATT ACA CAT GGC ATG GAT GAA CTA TAC AAA CTC GAG

Asn Ser Thr Met Gly Asp Val Glu Lys Gly Lys Lys Ile Phe Ile Met
721   AAT TCG ACC ATG GGT GAT GTT GAG AAA GGC AAG AAG ATT TTT ATT ATG

Lys Cys Ser Gln Cys His Thr Val Glu Lys Gly Gly Lys His Lys Thr
769   AAG TGT TCC CAG TGC CAC ACC GTT GAA AAG GGA GGC AAG CAC AAG ACT

Gly Pro Asn Leu His Gly Leu Phe Gly Arg Lys Thr Gly Gln Ala Pro
817   GGG CCA AAT CTC CAT GGT CTC TTT GGG CGG AAG ACA GGT CAG GCC CCT

Gly Tyr Ser Tyr Thr Ala Ala Asn Lys Asn Lys Gly Ile Ile Trp Gly
```

Figure 10 (continued)

```
865   GGA TAC TCT TAC ACA GCC GCC AAT AAG AAC AAA GGC ATC ATC TGG GGA

Glu Asp Thr Leu Met Glu Tyr Leu Glu Asn Pro Lys Lys Tyr Ile Pro
913   GAG GAT ACA CTG ATG GAG TAT TTG GAG AAT CCC AAG AAG TAC ATC CCT

Gly Thr Lys Met Ile Phe Val Gly Ile Lys Lys Lys Glu Glu Arg Ala
961   GGA ACA AAA ATG ATC TTT GTC GGC ATT AAG AAG AAG GAA GAA AGG GCA

Asp Leu Ile Ala Tyr Leu Lys Lys Ala Thr Asn Glu
1009  GAC TTA ATA GCT TAT CTC AAA AAA GCT ACT AAT GAG
```

Figure 11. SEQ ID NO: 8 - TriGFP-wild type cytochrome C

```
1
Met Ser Lys Gly Glu Glu Leu Phe Thr Gly Val Val Pro Ile Leu Val
17
Glu Leu Asp Gly Asp Val Asn Gly His Lys Phe Ser Val Ser Gly Glu
33
Gly Glu Gly Asp Ala Thr Tyr Gly Lys Leu Thr Leu Lys Phe Ile Cys
49
Thr Thr Gly Lys Leu Pro Val Pro Trp Pro Thr Leu Val Thr Thr Leu
65
Ser Tyr Gly Val Gln Cys Phe Ser Arg Tyr Pro Asp His Met Lys Arg
81
His Asp Phe Phe Lys Ser Ala Met Pro Glu Gly Tyr Val Gln Glu Arg
97
Thr Ile Phe Phe Lys Asp Asp Gly Asn Tyr Lys Thr Arg Ala Glu Val
113
Lys Phe Glu Gly Asp Thr Leu Val Asn Arg Ile Glu Leu Lys Gly Ile
129
Asp Phe Lys Glu Asp Gly Asn Ile Leu Gly His Lys Leu Glu Tyr Asn
145
Tyr Asn Ser His Asn Val Tyr Ile Met Ala Asp Lys Gln Lys Asn Gly
161
Ile Lys Val Asn Phe Lys Ile Arg His Asn Ile Glu Asp Gly Gly Val
177
Gln Leu Ala Asp His Tyr Gln Gln Asn Thr Pro Ile Gly Asp Gly Pro
193
Val Leu Leu Pro Asp Asn His Tyr Leu Ser Thr Gln Ser Ala Leu Ser
209
Lys Asp Pro Asn Glu Lys Arg Asp His Met Val Leu Leu Gly Phe Val
225
Thr Ala Ala Gly Ile Thr His Gly Met Asp Glu Leu Tyr Lys Leu Glu
241
Asn Ser Thr Met Gly Asp Val Glu Lys Gly Lys Lys Ile Phe Ile Met
257
Lys Cys Ser Gln Cys His Thr Val Glu Lys Gly Gly Lys His Lys Thr
273
Gly Pro Asn Leu His Gly Leu Phe Gly Arg Lys Thr Gly Gln Ala Pro
289
Gly Tyr Ser Tyr Thr Ala Ala Asn Lys Asn Lys Gly Ile Ile Trp Gly
305
Glu Asp Thr Leu Met Glu Tyr Leu Glu Asn Pro Lys Lys Tyr Ile Pro
321
Gly Thr Lys Met Ile Phe Val Gly Ile Lys Lys Lys Glu Glu Arg Ala
337
Asp Leu Ile Ala Tyr Leu Lys Lys Ala Thr Asn Glu
```

Figure 12. SEQ ID NO: 9 - Wild type Cytochrome C-triGFP

```
      Met Gly Asp Val Glu Lys Gly Lys Lys Ile Phe Ile Met Lys Cys Ser
  1   ATG GGT GAT GTT GAG AAA GGC AAG AAG ATT TTT ATT ATG AAG TGT TCC

Gln Cys His Thr Val Glu Lys Gly Gly Lys His Lys Thr Gly Pro Asn
 49   CAG TGC CAC ACC GTT GAA AAG GGA GGC AAG CAC AAG ACT GGG CCA AAT

Leu His Gly Leu Phe Gly Arg Lys Thr Gly Gln Ala Pro Gly Tyr Ser
 97   CTC CAT GGT CTC TTT GGG CGG AAG ACA GGT CAG GCC CCT GGA TAC TCT

Tyr Thr Ala Ala Asn Lys Asn Lys Gly Ile Ile Trp Gly Glu Asp Thr
145   TAC ACA GCC GCC AAT AAG AAC AAA GGC ATC ATC TGG GGA GAG GAT ACA

Leu Met Glu Tyr Leu Glu Asn Pro Lys Lys Tyr Ile Pro Gly Thr Lys
193   CTG ATG GAG TAT TTG GAG AAT CCC AAG AAG TAC ATC CCT GGA ACA AAA

Met Ile Phe Val Gly Ile Lys Lys Lys Glu Glu Arg Ala Asp Leu Ile
241   ATG ATC TTT GTC GGC ATT AAG AAG AAG GAA GAA AGG GCA GAC TTA ATA

Ala Tyr Leu Lys Lys Ala Thr Asn Glu Gly Arg Pro Gly Met Ser Lys
289   GCT TAT CTC AAA AAA GCT ACT AAT GAG GGT CGA CCC GGG ATG AGT AAA

Gly Glu Glu Leu Phe Thr Gly Val Val Pro Ile Leu Val Glu Leu Asp
337   GGA GAA GAA CTT TTC ACT GGA GTT GTC CCA ATT CTT GTT GAA TTA GAT

Gly Asp Val Asn Gly His Lys Phe Ser Val Ser Gly Glu Gly Glu Gly
385   GGT GAT GTT AAT GGG CAC AAA TTT TCT GTC AGT GGA GAG GGT GAA GGT

Asp Ala Thr Tyr Gly Lys Leu Thr Leu Lys Phe Ile Cys Thr Thr Gly
433   GAT GCA ACA TAC GGA AAA CTT ACC CTT AAA TTT ATT TGC ACT ACT GGA

Lys Leu Pro Val Pro Trp Pro Thr Leu Val Thr Thr Leu Ser Tyr Gly
481   AAA CTA CCT GTT CCA TGG CCA ACA CTT GTC ACT ACT CTC TCT TAT GGT

Val Gln Cys Phe Ser Arg Tyr Pro Asp His Met Lys Arg His Asp Phe
529   GTT CAA TGC TTT TCA AGA TAC CCA GAT CAT ATG AAA CGG CAT GAC TTT

Phe Lys Ser Ala Met Pro Glu Gly Tyr Val Gln Glu Arg Thr Ile Phe
577   TTC AAG AGT GCC ATG CCC GAA GGT TAT GTA CAG GAA AGA ACT ATA TTT

Phe Lys Asp Asp Gly Asn Tyr Lys Thr Arg Ala Glu Val Lys Phe Glu
625   TTC AAA GAT GAC GGG AAC TAC AAG ACA CGT GCT GAA GTC AAG TTT GAA

Gly Asp Thr Leu Val Asn Arg Ile Glu Leu Lys Gly Ile Asp Phe Lys
673   GGT GAT ACC CTT GTT AAT AGA ATC GAG TTA AAA GGT ATT GAT TTT AAA

Glu Asp Gly Asn Ile Leu Gly His Lys Leu Glu Tyr Asn Tyr Asn Ser
721   GAA GAT GGA AAC ATT CTT GGA CAC AAA TTG GAA TAC AAC TAT AAC TCA

His Asn Val Tyr Ile Met Ala Asp Lys Gln Lys Asn Gly Ile Lys Val
769   CAC AAT GTA TAC ATC ATG GCA GAC AAA CAA AAG AAT GGA ATC AAA GTT

Asn Phe Lys Ile Arg His Asn Ile Glu Asp Gly Gly Val Gln Leu Ala
817   AAC TTC AAA ATT AGA CAC AAC ATT GAA GAT GGA GGC GTT CAA CTA GCA

Asp His Tyr Gln Gln Asn Thr Pro Ile Gly Asp Gly Pro Val Leu Leu
```

Figure 12 (continued)

```
865 GAC CAT TAT CAA CAA AAT ACT CCA ATT GGC GAT GGC CCT GTC CTT TTA

Pro Asp Asn His Tyr Leu Ser Thr Gln Ser Ala Leu Ser Lys Asp Pro
913 CCA GAC AAC CAT TAC CTG TCC ACA CAA TCT GCC CTT TCG AAA GAT CCC

Asn Glu Lys Arg Asp His Met Val Leu Leu Gly Phe Val Thr Ala Ala
961 AAC GAA AAG AGA GAC CAC ATG GTC CTT CTT GGC TTT GTA ACA GCT GCT

Gly Ile Thr His Gly Met Asp Glu Leu Tyr Lys
1009 GGG ATT ACA CAT GGC ATG GAT GAA CTA TAC AAA
```

Figure 13. SEQ ID NO: 10 - Wild Type Cytochrome C-triGFP

```
  1
Met Gly Asp Val Glu Lys Gly Lys Lys Ile Phe Ile Met Lys Cys Ser
 17
Gln Cys His Thr Val Glu Lys Gly Gly Lys His Lys Thr Gly Pro Asn
 33
Leu His Gly Leu Phe Gly Arg Lys Thr Gly Gln Ala Pro Gly Tyr Ser
 49
Tyr Thr Ala Ala Asn Lys Asn Lys Gly Ile Ile Trp Gly Glu Asp Thr
 65
Leu Met Glu Tyr Leu Glu Asn Pro Lys Lys Tyr Ile Pro Gly Thr Lys
 81
Met Ile Phe Val Gly Ile Lys Lys Lys Glu Glu Arg Ala Asp Leu Ile
 97
Ala Tyr Leu Lys Lys Ala Thr Asn Glu Gly Arg Pro Gly Met Ser Lys
113
Gly Glu Glu Leu Phe Thr Gly Val Val Pro Ile Leu Val Glu Leu Asp
129
Gly Asp Val Asn Gly His Lys Phe Ser Val Ser Gly Glu Gly Glu Gly
145
Asp Ala Thr Tyr Gly Lys Leu Thr Leu Lys Phe Ile Cys Thr Thr Gly
161
Lys Leu Pro Val Pro Trp Pro Thr Leu Val Thr Thr Leu Ser Tyr Gly
177
Val Gln Cys Phe Ser Arg Tyr Pro Asp His Met Lys Arg His Asp Phe
193
Phe Lys Ser Ala Met Pro Glu Gly Tyr Val Gln Glu Arg Thr Ile Phe
209
Phe Lys Asp Asp Gly Asn Tyr Lys Thr Arg Ala Glu Val Lys Phe Glu
225
Gly Asp Thr Leu Val Asn Arg Ile Glu Leu Lys Gly Ile Asp Phe Lys
241
Glu Asp Gly Asn Ile Leu Gly His Lys Leu Glu Tyr Asn Tyr Asn Ser
257
His Asn Val Tyr Ile Met Ala Asp Lys Gln Lys Asn Gly Ile Lys Val
273
Asn Phe Lys Ile Arg His Asn Ile Glu Asp Gly Gly Val Gln Leu Ala
289
Asp His Tyr Gln Gln Asn Thr Pro Ile Gly Asp Gly Pro Val Leu Leu
305
Pro Asp Asn His Tyr Leu Ser Thr Gln Ser Ala Leu Ser Lys Asp Pro
321
Asn Glu Lys Arg Asp His Met Val Leu Leu Gly Phe Val Thr Ala Ala
337
Gly Ile Thr His Gly Met Asp Glu Leu Tyr Lys
```

CYTOCHROME C PROTEIN AND ASSAY

TECHNICAL FIELD

The present invention relates to a cytochrome c-reporter fusion protein construct which targets the mitochondria and has a reduced ability to induce apoptosis in a living cell. The fusion construct of the invention can be used in assays for detecting early events in apoptosis in living cells.

BACKGROUND TO THE INVENTION

'Programmed cell death' or apoptosis is a key event in multicellular organisms, defining a genetically encoded cell death program which is morphologically, biochemically and molecularly distinct from necrosis (Vermes et al., J Immunol Meth., (2000) 243, 167-190). The characteristic morphological signs of apoptosis (cellular shrinkage, membrane blebbing, nuclear condensation and fragmentation) are the results of a complex biochemical cascade of events which is an integral part of physiological homeostasis.

Apoptosis ensures an equilibrium between cell proliferation and cell death, thus playing a regulatory role in the control of the size of cell populations and tissues. Aberrations in cell death signalling, in membrane or cytoplasmic receptors, or alterations in genes that govern apoptosis are involved in the pathogenesis of congenital malformations and many acquired diseases (Haanen & Vermes, Eur J. Obstetr. Gynecol., (1996) 64, 129-133). Too little apoptosis may result in malignancies (Tomlinson & Bodmer, Proc. Natl. Acad. Sci. USA, (1995) 92, 11130-11134), Leukemias (Sachs, Proc. Natl. Acad. Sci. USA, (1996) 93, 4742-4749) or the resistance to anticancer therapy (Pahor et al., Lancet, (1996) 348, 493-497). Too much apoptosis can result in immune deficiency (Meyaard et al., Science (1992) 257, 217-219) and degenerative conditions (Griffith et al., Science, (1995) 270, 1189-1192).

There is therefore considerable interest within the medical, pharmaceutical and toxicological sciences in developing a greater understanding of the events which trigger and regulate apoptosis. Furthermore, there is a need to develop new techniques which can be used to identify, quantify and characterise agents which can modulate this phenomenon.

Assays for Detecting Apoptosis

A large number of assays have been developed to detect the onset of programmed cell death (Sgone & Wick, Int Arch Allergy Immunol., (1994) 105, 327-332; Sgone & Gruber, Exp Gerontol., (1998) 33, 525-533). These assays are based upon a wide range of events associated with cell death and have traditionally included light and electron microscopy with vital staining and nuclear dyes. Biochemical methods are often employed, for example based upon DNA laddering or degradation, DNA end labelling techniques (e.g. TUNEL—terminal deoxynucleotide transferase dUTP Nick End labelling), nuclease activity and lactate dehydrogenase enzyme release.

Flow cytometry tends to be the most widely used method (Vermes et al., J Immunol Methods, (2000) 243, 167-190) for detecting and quantifying apoptosis because it is amenable to screening large numbers of cells. This fluorescence—based technique employs vital dyes, antibodies to apoptotic enzymes (e.g. caspases) and single stranded DNA breaks, together with probes for measuring calcium flux and phospholipid redistribution.

Flow cytometry allows in vivo analysis of cells in suspension, one at a time, at rates of 1000 to 10,000 cells/s. However, one problem with flow cytometry is that it can only be used in cells in suspension, such as liquid cell cultures and cells derived from the hemopoietic system. Furthermore flow cytometry of tissue cells requires physical and enzymatic manipulation to get the cells in suspension, which by itself may trigger apoptosis, necessitating checks by conventional light or fluorescence microscopy.

Existing methods are thus based upon late events in apoptosis (e.g. DNA degradation, caspase assays) and many require cellular fixation and staining with specific antibodies/dyes. None of the techniques described above provide a homogeneous living cell assay, based upon the early events in apoptosis, in real time nor discriminate from cellular necrosis. Furthermore, none of these assays are amenable to high throughput live cell screening which is required to test large numbers of compounds for their ability to modulate apoptosis.

Cytochrome c Translocation as a Marker for Apoptosis

Cytochrome c is a nuclear encoded protein which is targeted to the mitochondria where it performs its biological function as an electron carrier. The translocation of cytochrome c from the mitochondria to the cytoplasm in response to apoptotic stimuli is an early and critical step in the commitment of the cell to undergo apoptosis (Li et al., Cell (1997) 91, 479-489). Cytochrome c binds strongly to apoptosis protease activation factor-1 (Apaf-1) in the cytosol (Zou et al., Cell (1997) 90, 405-413). In the presence of cofactors the resulting cytochrome c: Apaf-1 assembles into a multimeric 'apoptosome' that binds and activates a protease zymogen, procaspase-9 (Srinivasula et al., Mol. Cell (1998) 1, 949-957). This results in the activation of the 'caspase cascade' whereby many intracellular substrates are cleaved disabling important cellular processes and breaking down structural components of the cell (Slee et al., J Cell. Biol. (1999) 144, 281-292; Skulachev, FEBS Lett., (1998) 423, 275-280). A schematic diagram illustrating the mitochondrial role in apoptosis is shown in FIG. 1.

Recent in vitro studies (Kluck et al., J. Biol. Chem., (2000), 275, 16127-16133; Yu et al., J. Biol. Chem., (2001), 276, 1304-13038) have identified the molecular determinants involved in the cytochrome c: Apaf-1 interaction. Horse cytochrome c has been shown to be highly homologous to human cytochrome c and can initiate caspase activation, whereas yeast cytochrome c did not measurably bind to Apaf-1 nor activate caspase (Yu et al., J Biol Chem., (2001) 276, 13034-13038). These studies focussed on the key differences between horse and yeast cytochrome c and used site directed mutagenesis to generate mutant variants which were subsequently analysed with respect to their ability to activate caspase. The results from this in vitro work indicated that residue 7, 25, 39, 62-65 and 72 were critical amino acids for cytochrome c:Apaf-1 interaction. Notably the mutation K72A showed no detectable binding or caspase-9 activation. While the mutation of lysine 72 to alanine abolished the interaction between cytochrome c and Apaf1, respiratory function of cytochrome c was unaffected.

Although the authors demonstrated reduced binding to Apaf-1 and caspase-9 activation in vitro it is not known whether the cytochrome c mutant proteins would behave in a similar manner in living cells, targeting the mitochondria and not inducing apoptosis.

Recent reports by Abdullaev et al. (Biochem J. (2002) 362, 749-754), again based on in vitro experiments, indicate that the horse K72 mutants described by Yu et al. (J Biol Chem., (2001) 276, 13034-13038) show the same level of caspase activation as the wild-type protein if present at 2-12 fold higher concentrations than the wild type protein. In contrast, the authors reported that a horse K4E cytochrome c mutant was inactive in activating caspase and conclude that this mutant, rather than K72 mutants, would be a good candidate for in vivo knock-in studies on the role of cytochrome c in apoptosis.

Fluorescent Proteins

The use of Green Fluorescent Protein (GFP) derived from *Aequorea victoria* is now well known for research into many cellular and molecular-biological processes. Cytochrome c-GFP fusions have been used in studies on apoptosis. Thus Heiskanen et al. (J Biol Chem., (1999) 274, 5654-5658) expressed a cytochrome c-GFP fusion, based upon rat cytochrome c, in rat pheochromocytoma-6 (PC6) cells. Induction of apoptosis by staurosporine led to release of the fusion from the mitochondria which was accompanied by mitochondrial depolarisation.

Goldstein et al., (Nat Cell Bio., (2000) 2, 156-160) demonstrated mitochondrial localisation of a cytochrome c-GFP fusion, based upon human cytochrome c, over-expressed in HeLa cells. A range of apoptotic inducers were shown to cause rapid release of cytochrome c-GFP.

Other researchers have also used cells which have been transiently transfected to over-produce cytochrome c-GFP fusion proteins to investigate apoptosis. Thus Goa et al., (J. Cell Sci., (2001) 114, 2855-2862) monitored the dynamic redistribution of GFP-tagged cytochrome c and the morphological changes of mitochondria within living HeLa cells during UV-induced apoptosis. Similarly, Lim et al., (J Biomed Sci (2002); 9, 488-506) explored the biochemical basis of cytochrome c-GFP localisation by transiently transfecting COS-7 cells with various GFP constructs and determining sub-cellular distribution using fluorescence and immunochemical techniques.

Problem to be Addressed

There is a need to develop sensitive assays which are amenable to high throughput screening in living cells and which allow detection and analysis in real time of the early events in apoptosis.

While over-expression of cytochrome c in cells has been demonstrated, the resulting high levels of protein lead to apoptosis and cell death, necessitating the use of complex inducible/transient systems for studies involving up-regulation of cytochrome c levels (Chandra et al., J Biol Chem. (2002) 277, 50842-50854). To date, it has not been possible to generate stable cell lines over-expressing this protein which could be reliably used for screening purposes.

There is thus a need for a cytochrome c protein which, when coupled to a reporter group to form a fusion construct, can be expressed in cells to provide stable cell lines. The resulting construct can act as a biosensor within the cells for early events in the induction or repression of apoptosis. Stable cell lines overexpressing such constructs are suitable for high throughput screening purposes to identify agents which modulate apoptosis.

The present invention addresses this problem and provides a fusion construct which has no observable toxicity to cells and acts as a biosensor to permit the detection of early events in apoptosis in living cells. The stably transformed cells of the invention can still undergo apoptosis due to the presence of endogenous cytochrome c, thus allowing detection and determination of a second apoptotic signaling event whether up or downstream of the cytochrome c translocation.

SUMMARY OF THE INVENTION

In a first aspect of the present invention there is provided a cytochrome c-reporter fusion protein construct comprising a modified cytochrome c protein or any functional analogue thereof derived from wild type cytochrome c, wherein the modified cytochrome c targets the mitochondria and has a reduced ability to induce apoptosis in a living cell.

A reporter is to be understood to be any group that is detectable due to its radioactive, fluorescent or luminescent properties or is localisable by a detectable moiety such as a labeled antibody or specific binding compound.

Preferably, the modified cytochrome c binds apoptosis protease activation factor-1 (Apaf-1) at least 10 times less than wild type cytochrome c. More preferably, the modified cytochrome c binds Apaf-1 at least 100 times less than wild type cytochrome c. Most preferably, the modified cytochrome c binds Apaf-1 at least 1000 times less than wild type cytochrome c.

Suitably, at least one of the amino acids of the modified cytochrome c at positions 4, 7, 8, 25, 39, 62, 63, 64, 65 and 72 has been mutated relative to the wild type cytochrome c.

Suitably, the modified cytochrome c has an amino substitution or substitutions selected from the group consisting of K4E, K72A, K72L, K72R, K72G, K72X, E62N, K7E-K8E, K25P-K39H, K7A-E62N-K25P, K7A-E62N-K39H, K7E-K8E-E62N, K7A-K25P-E62N, K7A-E62N-K25P-K39H, E62N-T63N-L64M-M65S, K7E-K8E-E62N-K25P-K39H, K7E-K8E-K25P-E62N-T63N-L64M-M65S, K7E-K8E-K39H-E62N-T63N-L64M-M65S and K7E-K8E-K25P-K39H-E62N-T63N-L64M-M65S.

Preferably, the modified cytochrome c comprises the amino acid substitution selected from the group consisting of K7E-K8E-E62N-K25P-K39H, K7E-K8E-K25P-E62N-T63N-L64M-M65S, K7E-K8E-K39H-E62N-T63N-L64M-M65S and K7E-K8E-K25P-K39H-E62N-T63N-L64M-M65S.

More preferably, the modified cytochrome c comprises the amino acid substitution selected from the group consisting of K72A, K72L, K72R, K72G and K72X, wherein X represents trimethylation. Most preferably, the modified cytochrome c comprises the amino acid substitution K72A or K72L.

Preferably, modified cytochrome c comprises the amino acid substitution K4E.

Suitably, the reporter is a fluorescent protein or a functional analogue thereof.

It will be understood by the person skilled in the art that a functional analogue of a fluorescent protein will include, but is not limited to, any detectable fluorescent protein fragment formed in a protein fragment complementation assay as described, for example, in U.S. Pat. Nos. 6,270,964, 6,428, 951 and 6,294,330.

Preferably, the fluorescent protein of the present invention is a Green Fluorescent Protein (GFP) derived from *Aequoria victoria, Renilla reniformis* or other members of the class *Anthozoa* (Labas et al., Proc. Natl. Acad. Sci, (2002), 99, 4256-4261).

U.S. Pat. No. 6,172,188 describes variant GFPs wherein the amino acid in position 1 preceding the chromophore has been mutated to provide an increase in fluorescence intensity. These mutants result in a substantial increase in the intensity of fluorescence of GFP without shifting the excitation and emission maxima. F64L-GFP has been shown to yield an approximate 6-fold increase in fluorescence at 37° C. due to shorter chromophore maturation time.

One mutant, commonly termed Enhanced Green Fluorescent Protein (EGFP), contains the mutations F64L and S65T (Cormack, B. P. et al., Gene, (1996), 173, 33-38). EGFP has been optimised for expression in mammalian systems, having been constructed with preferred mammalian codons.

Suitably, the fluorescent protein is selected from the group consisting of Green Fluorescent Protein (GFP), Yellow Fluorescent Protein (YFP), Blue Fluorescent Protein (BFP), Cyan Fluorescent Protein (CFP), Red Fluorescent Protein (RFP), Enhanced Green Fluorescent Protein (EGFP) and Emerald. Preferably, the fluorescent protein is either EGFP or Emerald.

GB 2374868 describes GFP derivatives having a triple mutation at F64, S65/E222 and S175 which exhibit enhanced fluorescence relative to wild type GFP when expressed in non-homologous cells at temperatures above 30° C. and when excited at about 490 nm. Mutant GFPs produced using the method of the invention provide a means for detecting GFP reporters in mammalian cells at lower levels of expression and/or increased sensitivity relative to wild type GFP.

Preferably, the GFP of the present invention comprises
  i) an amino acid substitution at position F64L;
  ii) an amino acid substitution at position S175G; and
  iii) an amino acid substitution at position E222G.

In a preferred embodiment the fusion construct is either SEQ ID NO: 4 or SEQ ID NO: 6.

In one embodiment, the reporter is localisable by a detectable luminescent, fluorescent or radio-active moiety. Thus, for example, the reporter comprises an immunogenic motif and the detectable moiety may be a luminescent, fluorescent or radio-actively labeled antibody.

Suitably, the reporter comprises a FLAG™, HA, HIS, c-Myc, VSV-G, V5 or a HSV (Sigma-Aldrich) epitope which is localisable by specific labeled antibodies.

In another embodiment, the reporter comprises a cysteine-rich motif and the detectable moiety comprises a labeled biarsenical compound as described by Griffin et al., Science (1998), 281, 269-272) and in U.S. Pat. Nos. 6,054,271, 6,008,378 and 5,932,474.

In a second aspect of the present invention, there is provided a nucleotide sequence encoding a protein fusion construct as hereinbefore described.

Preferably the nucleotide sequence is SEQ ID NO: 3 or SEQ ID NO: 5.

In a third aspect of the present invention, there is provided a nucleic acid construct comprises a suitable control region and the nucleotide sequence as hereinbefore described, the sequence being under the control of the control region.

Suitably, the nucleic acid construct is under the control of a promoter selected from the group consisting of native cytochrome c promoter, mammalian constitutive promoter, mammalian regulatory promoter, human ubiquitin C promoter, viral promoter, SV40 promoter, CMV promoter, yeast promoter, filamentous fungal promoter and bacterial promoter.

Preferably, the promoter is the CMV or the SV40 promoter. More preferably, the promoter is the human ubiquitin C promoter.

In a fourth aspect of the present invention, there is provided a replicable vector comprising a nucleic acid construct as hereinbefore described.

Suitably, the vector is a plasmid vector as described by Makrides (Prot Expression & Purif. (1999) 17, 183-202).

Preferably the vector is a viral vector. Suitable viral vectors for use in the invention are described, for example, by Ng et al., Hum Gene Ther. (2000) 11, 693-699 and include cytomegalovirus, Herpes simplex virus, Epstein-Barr virus, Simian virus 40, Bovine papillomavirus, Adeno-associated virus, Adenovirus, Vaccina virus and Baculovirus vector.

In a fifth aspect of the present invention, there is provided a host cell stably transformed with a nucleic acid construct as hereinbefore described.

In a sixth aspect of the present invention, there is provided a host cell transiently transformed with a nucleic acid construct as hereinbefore described.

Suitably, the host cell is selected from the group consisting of plant, insect, nematode, bird, fish and mammalian cell. Preferably the cell is a human cell. More preferably the human cell is selected from the group consisting of Hek, Hela, U2OS and MCF-7. Most preferably the cell is Hek cell line 293 (Hek293).

Suitably, the host cell is capable of expressing the fusion protein as hereinbefore described.

In a seventh aspect of the present invention, there is provided a method for detecting apoptosis in a living cell comprising the steps of
  i) culturing a cell transformed to over-express a fusion construct as hereinbefore described;
  ii) determining the localisation of the fusion construct within the cell with time;
wherein a change in localisation of the fusion construct within the cell is indicative of apoptosis.

In an eighth aspect of the present invention, there is provided a method for measuring the effect an agent has upon modulating apoptosis in a living cell comprising the steps of
  i) culturing a cell transformed to over-express a fusion construct as hereinbefore described;
  ii) determining the localisation of the construct within the cell;
  iii) treating the cell with the agent and determining the localisation of the construct within the cell;
wherein any difference in the localisation of the construct within the cell relative to control cells untreated with the agent is indicative of the effect the agent has upon modulating apoptosis.

In a ninth aspect of the present invention, there is provided a method for measuring the effect an agent has upon modulating apoptosis in a living cell comprising the steps of
  i) culturing a first cell and a second cell which both over-express a fusion construct as hereinbefore described;
  ii) treating the first cell with the agent and determining the localisation of the construct within the first cell;
  iii) determining the localisation of the construct within the second cell which has not been treated with the agent;
wherein any difference in the localisation of the construct within the first cell and second cell is indicative of the effect the agent has upon modulating apoptosis.

In a tenth aspect of the present invention, there is provided a method for measuring the effect an agent has upon modulating apoptosis in a living cell comprising the steps of
  i) culturing a cell transformed to over-express a fusion construct as hereinbefore described;
  ii) treating the cell with the agent and determining the localisation of the construct within the cell;
  iii) comparing the localisation of the construct in the presence of the agent with a known value for the localisation of the construct in the absence of the agent;
wherein any difference in the localisation of the construct within the cell in the presence of the agent and the known value in the absence of the agent is indicative of the effect the agent has upon modulating apoptosis.

Suitably, the known value according is stored on a database, such as an electronic or optical database.

Suitably, the localisation of the protein fusion is measured by its luminescence, fluorescence or radioactive properties.

The method of the invention is suitable for screening purposes to identify agents which induce or inhibit apoptosis.

In another embodiment of the method of the invention, the localisation of the fusion construct is determined on non-living, fixed cells. Thus, the living cells over-expressing the fusion construct are fixed at specific time points by conventional means and the location of the fusion protein detected using a detectable moiety, such as a labeled antibody or specific binding chemical. In this way, the effect an agent has upon apoptosis can be determined by comparing localisation of the fusion construct in the presence and the absence of the agent. Alternatively, the effect that the agent has upon apoptosis can be determined by comparing localisation of the construct in the presence of the agent against a known value (for example, one stored on a database) for localisation in the absence of the agent.

Suitably, the agent is a chemical, physical or biological agent. Examples of chemical agents include inorganic and organic compounds, such as drugs, toxins, peptides, proteins and nucleic acids. Physical agents include electromagnetic radiation such as electrical, magnetic and light (UV, gamma, IR, visible) energy. Examples of typical biological agents include viruses, prions, bacteria and fungi which could infect a living cell and modulate apoptosis.

BRIEF DESCRIPTION OF THE DRAWINGS

FIG. 3a) Cytochrome c (K72A)-GFP

FIG. 4. Nucleic acid sequence encoding wild type cytochrome c (SEQ ID NO: 1)

FIG. 5. Amino acid sequence of wild type cytochrome c (SEQ ID NO: 2)

FIG. 6. Nucleic acid sequence encoding F64L-S175G-E222G-triGFP-cytochrome c (K72A) construct (SEQ ID NO: 3)

FIG. 7. Amino acid sequence of F64L-S175G-E222G-triGFP-cytochrome c (K72A) construct (SEQ ID NO: 4)

FIG. 8. Nucleic acid sequence encoding cytochrome c (K72A)-F64L-S175G-E222G-triGFP (SEQ ID NO: 5)

FIG. 9. Amino acid sequence of cytochrome c (K72A)-F64L-S175G-E222G-triGFP (SEQ ID NO: 6)

FIG. 10. Nucleic acid sequence encoding F64L-S175G-E222G-wild type cytochrome c construct (SEQ ID NO: 7)

FIG. 11. Amino acid sequence of F64L-S175G-E222G wild type cytochrome c construct (SEQ ID NO: 8)

FIG. 12. Nucleic acid sequence encoding wild type cytochrome c-F64L-S175G-E222G tri GFP (SEQ ID NO: 9)

FIG. 13. Amino acid sequence of wild type cytochrome c-F64L-S175G-E222G tri GFP (SEQ ID NO: 10)

Figure 1:
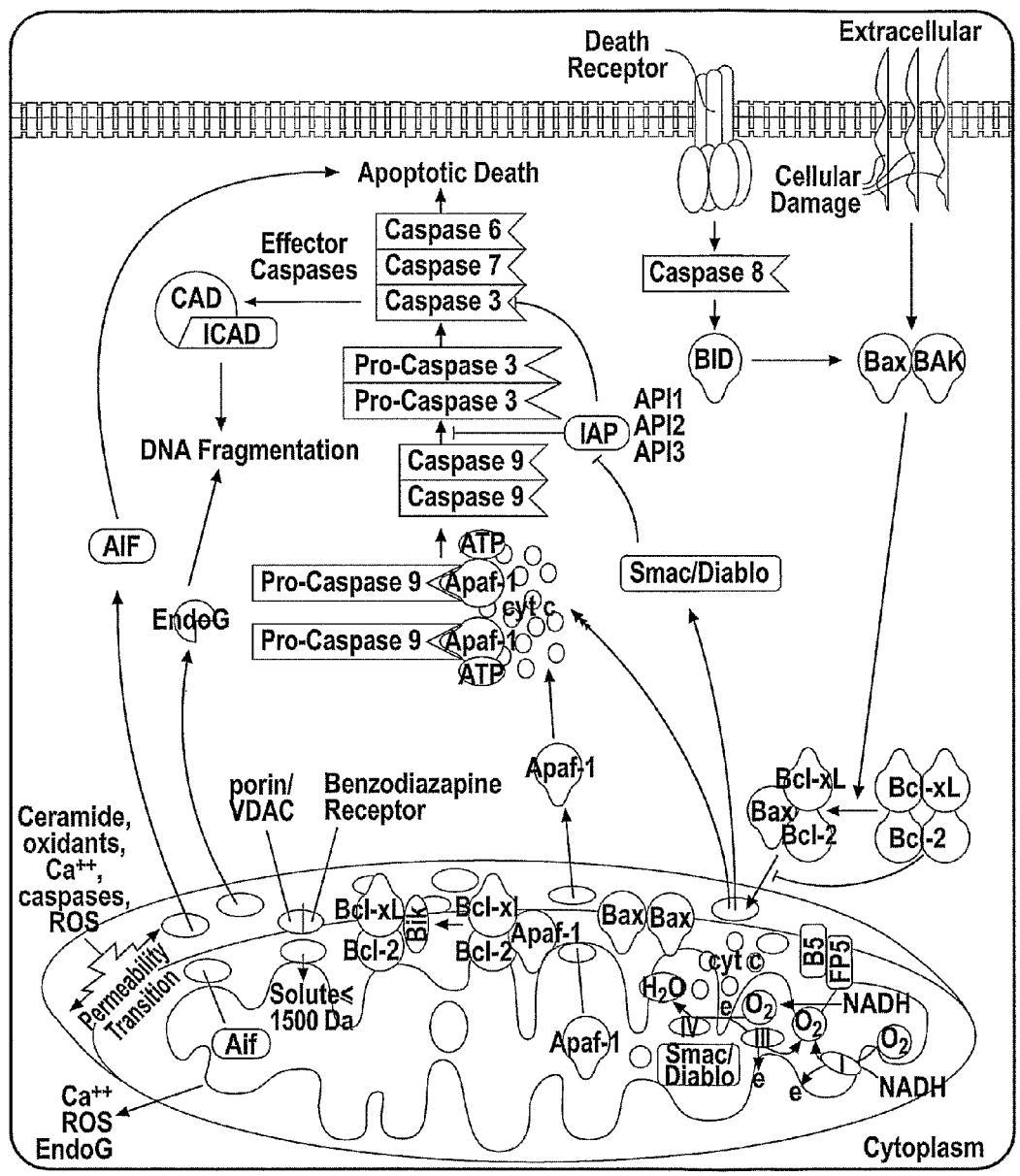
FIG. 1. Schematic representation depicting the mitochondrial role in apoptosis; reproduced by kind permission of Biocarta: (www.biocarta.com/pathfiles/h_mitochondriaPathway.asp).

The file of this patent contains at least one drawing executed in color. Copies of this patent with color drawing(s) will be provided by the Patent and Trademark Office upon request and payment of the necessary fee.

SPECIFIC EXAMPLES

Example 1

Amplification of the cytochrome c gene, fusion to GFP (F64L-S175G-E222G) and introduction of the K72A (APAF-1 binding) mutation.

The fluorescent-cytochrome c mutant fusion proteins of the current invention were produced by joining, in frame, a sequence of the nucleic acid that encodes for the cytochrome c protein to a sequence of the nucleic acid that encodes for a fluorescent protein and then introducing the K72A (APAF-1 binding) mutation (Kluck et al., J Biol Chem., (2000) 275, 16127-16133)) to the nucleic acid of the fusion construct. A preferred sequence of the human cytochrome c gene is described by Zang and Gerstein (Gene, (2003) 312, 61-72); NCBI Accession number NM_018947. (SEQ ID NO: 1) the encoded protein is shown in SEQ ID NO: 2. Alternative human cytochrome c sequences may be used. In addition, alternative sequences around the start and stop codons of the gene may be used to provide useful restriction enzyme sites for protein fusion. Where such alterations change the amino acid numbering relative to the reference sequence such numbering should be inferred by amino acid alignment with the reference sequence. Preferred sequences of the gene encoding the fluorescent protein include those derived from *Aequorea victoria* published by Chalfie et al, (Science, (1994) 263, 802-5), the GFP-F64L-S175G-E222G mutant (GB Patent 2374868), Emerald (*Aurora biosciences*), EGFP and related mutants (BD Clontech, Palo Alto, Calif.), and fluorescent proteins from species of *Anthazoa*, for review see Labas et al, (PNAS, (2002) 99, 4256-4261).

The cytochrome c gene was amplified by RT-PCR from a mixed human cDNA library using primers CYCS1 and CYCS2 or CYCS1 and CYCS3 according to recognised protocols (Sambrook, J. et al (2001) Molecular Cloning—A Laboratory Manual, Cold Spring Harbor Laboratory Press).

```
                                         (SEQ ID NO: 11)
CYCS1; 5'-gttgaattcgaccatgggtgatgttgagaaaggc (SEQ ID NO: 12)
CYCS2; 5'-gttgttgtcgaccttactcattagtagctttttgag (SEQ ID NO: 13)
CYCS3; 5'-gttgttgtcgaccctcattagtagctttttgag
```

Primer CYCS1 exhibits homology to the 5' region of the cytochrome c gene and contains both a partial Kozak sequence (Kozak, Cell (1986), 44, 283) and an EcoR1 restriction enzyme site. Primer CYCS2 exhibits homology to the 3' region of the cytochrome c gene and contains a stop codon and SalI restriction enzyme site. Primer CYCS3 exhibits homology to the 3' region of the cytochrome c gene and contains a SalI restriction enzyme site. The CYCS1-CYCS2 and CYCS1-CYCS3 RT-PCR products were cloned into the corresponding EcoRI and SalI sites of the GFP-fusion vectors pCORON1000-GFP-C1 and N1, respectively (Amersham Biosciences, Cardiff, UK) and verified by automated sequencing. These vectors contain a CMV promoter to effect the expression of the GFP fusion and an SV40 promoter to elicit expression of a neomycin resistance marker. The GFP within these vectors is red-shifted and contains the mutations F64L-S175G-E222G as described in GB 2374868.

Cytochrome c (K72A) mutants were generated with the QuikChange™ site-directed mutagenesis kit (Stratagene, La Jolla, Calif., USA) using primers CYCS4 and CYCS5.

```
                                              (SEQ ID NO: 14)
CYCS4; 5'-ggagtatttggagaatcccgccaagtacatccctggaacaa (SEQ ID NO: 15)
CYCS5; 5'-ttgttccagggatgtacttggcgggattctccaaatactcc
```

After sequence verification the pCORON1000-GFP-wild type cytochrome c and K72A mutant fusion constructs were sub-cloned into the vector pCORON2100 using the restriction enzymes NheI and NotI. pCORON2100 contains a CMV promoter and an IRES element to drive bicistronic expression of the GFP-fusion protein and a neomycin resistance marker.

The nucleic acid and amino acid sequences of the GFP-cytochrome c constructs obtained are shown in FIGS. 6 to 13 (SEQ ID NOS: 3-10)

Example 2

Influence of cytochrome c-K72A (APAF-1 binding) mutation upon GFP-fusion protein stable cell line generation in mammalian cells.

Plasmid DNA to be used for transfection was prepared for all constructs using the HiSpeed plasmid purification kit (Qiagen, Westberg, NL). In addition to the constructs in example 1, pCORON1000-GFP and pCORON2100-GFP were used as selection controls. DNA was diluted to 100 ng. $\mu l^{-1}$ in 18-Megohm water (Sigma, Dorset, UK) and 1 μg used for transfections. For 50-80% confluency on the day of transfection, Hek293 cells were plated at a density of $5 \times 10^4$/well in 6-well plates and incubated overnight. A 1:3 (1 μg:3 μl) ratio of DNA to FuGene6 reagent (Roche Diagnostics, Basel, Switzerland) was used for each transient transfection reaction; 3 μl FuGene6 was added to 87 μl serum-free DMEM medium (Sigma) (containing penicillin/streptomycin, L-glutamine [Invitrogen, Carlsbad, Calif.]) and gently tapped to mix, then 10 μl (1 μg) construct DNA was added and again gently mixed. The FuGene6: DNA complex was incubated at room temperature for 40 minutes and added dropwise, with gentle mixing, directly to the cells without changing the medium. The plates were then gently swirled for even distribution. Cells were monitored for expression after 24 and 48 hours using a Nikon Eclipse TE200 epifluorescent microscope (Nikon, Melville, N.Y.). Cells were passed into 15 cm diameter plates and after 24 hours placed under selection with geneticin (G418, 250 ng. $\mu l^{-1}$; Sigma). The concentration of geneticin was increased incrementally to 500 ng. $\mu l^{-1}$ over the following 5-7 days. Selection continued for around 10 days or until cells in the mock-transfected control plates had died. Cloning rings were then used to isolate surviving colonies and cells were expanded through 96-well, 24-well and 6-well plates. Where appropriate second and third rounds of clonal selection were applied.

After the first round of clonal selection surviving cells were visible for transfections containing pCORON1000-GFP, pCORON2100-GFP and the pCORON2100-GFP-N and -C cytochrome c (K72A) mutant plasmids. No surviving colonies were obtained from cells transfected with other plasmid contructs.

Results

Expression studies of this mutated cDNA were performed in pCORON2100 (Amersham Biosciences) in order to utilise the IRES element and facilitate the generation of stable cell lines. A "mixed population" stably expressing cell line under selection with geneticin G418 was continuously cultured for 3 weeks. 15 single clonal cell lines were then isolated.

Hek293 cells containing the pCORON2100-GFP-cytochrome c (K72A) mutants were shown to exhibit stable expression during continuous culture over a 4 month period. The mitochondrial localisation of the reporter fusion proteins was confirmed during this period by co-localisation with the known mitochondrial marker mitotracker red (Molecular Probes, Eugene, Oreg.) using a Microsystems LSM (Zeiss, Thornwood, N.Y.) and a high throughput laser scanning confocal microscope (INCell Analyzer 3000, Amersham Biosciences).

Figure 2A:
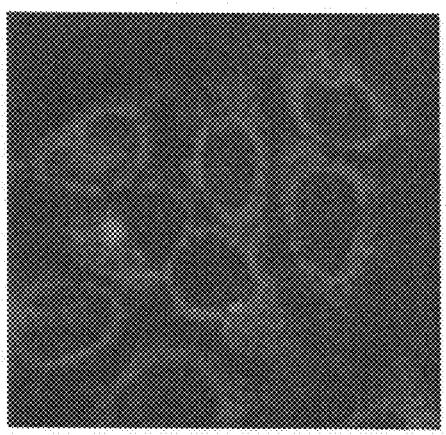
FIG. 2a) InCell Analyzer 3000 images (ca. 40× magnification) showing cytochrome c (K72A-GFP mutant) labeled mitochondria in Hek 293 cells of clone 2B6.
Figure 2B:
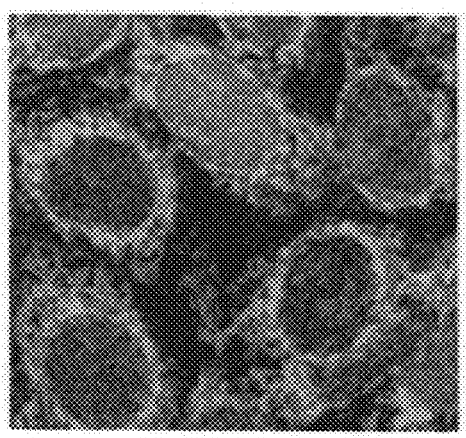
FIG. 2b) Confocal microscopic image (ca. 60×) cytochrome c-GFP expression in HeLa cells (from Goldstein et al., (Nat Cell Bio., (2000) 2, 156-160))

The expression results from one of these stable clones (2B6), using the InCell Analyzer 3000 (Amersham Biosciences, UK) laser scanning confocal imaging system, are shown below in FIG. 2. As can be seen from FIG. 2a the localisation pattern of expressed cytochrome c-GFP closely resembles that observed by Goldstein et al., (Nat Cell Bio., (2000) 2, 156-160), using a confocal microscope, reproduced in FIG. 2b. As expected, the fusion protein demonstrates nuclear exclusion and localises to mitochondria, the cytochrome c-GFP displaying a punctuate pattern of fluorescence (FIG. 2a).

Figure 3A:
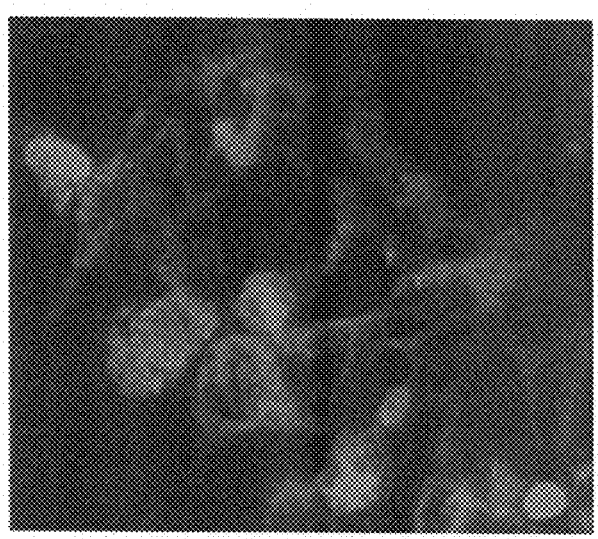
FIG. 3a)-c). InCell Analyzer 3000 images showing colocalisation of cytochrome c (K72A mutant)-GFP and Tetramethylrhodamine ethyl ester (TMRE) using dual excitation of cytochrome c and TMRE in Hek 293 cells.
Figure 3B:
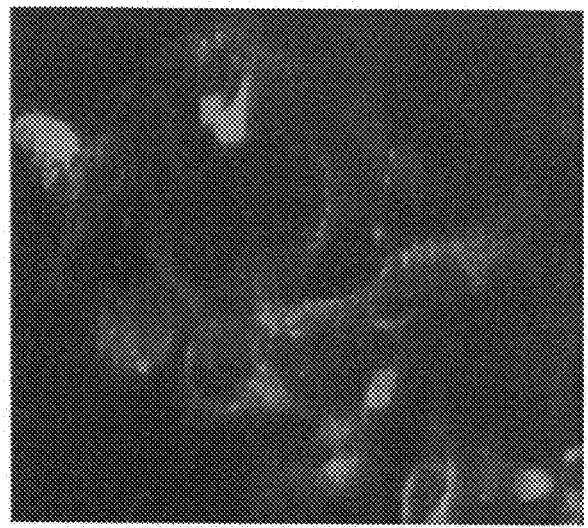
FIG. 3b) TMRE labeled mitochondria
Figure 3C:
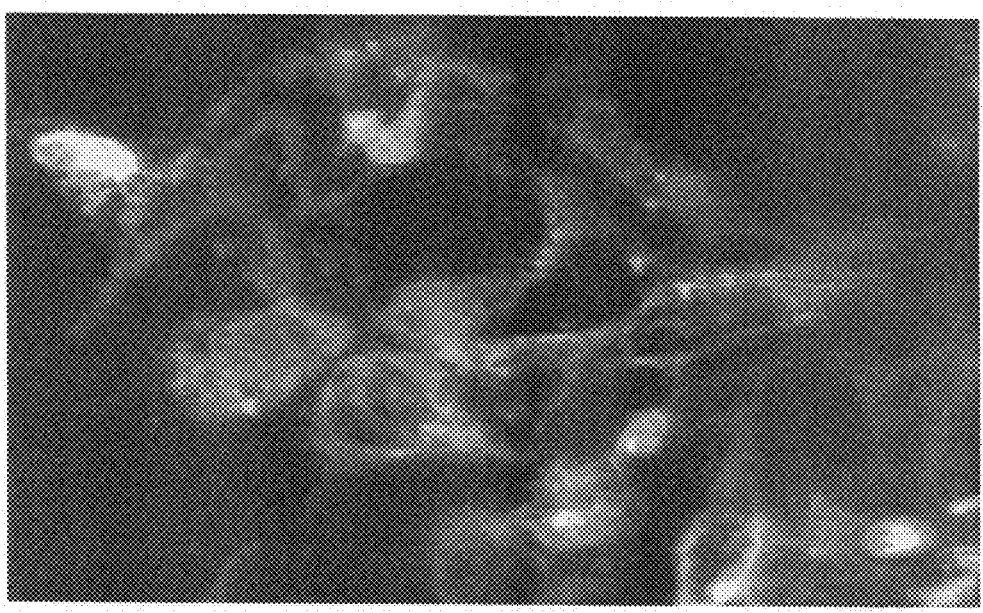
FIG. 3c) overlay of FIGS. 3a) & 3b) following dual excitation

FIGS. 3a and 3b show localisation of the fusion protein construct (a) and the mitochondrial stain TMRE (b) at a concentration of 40 nM in the mitochondria of Hek 293 cells. Dual excitation of the cytochrome c-GFP and TMRE in the InCell Analyzer demonstrates co-localisation (FIG. 3c).

The invention claimed is:

1. A cytochrome C-reporter fusion protein construct comprising:
   (a) a modified cytochrome C protein derived from wild type human cytochrome C represented by SEQ ID NO: 2; and
   (b) a fluorescent protein,
   wherein said fusion protein targets the mitochondria and has a reduced ability to induce apoptosis in a living cell, and
   wherein said modified cytochrome C comprises the amino acid substitution selected from the group consisting of K73A, K73L, K73R, K73G and K73X, wherein X represents trimethylation.

2. The fusion construct of claim 1, wherein said modified cytochrome C binds apoptosis protease activation factor-1 (Apaf-1) at least ten times less than wild type cytochrome C.

3. The fusion construct of claim 1, wherein said modified cytochrome C binds apoptosis protease activation factor-1 (Apaf-1) at least 100 times less than wild type cytochrome C.

4. The fusion construct of claim 1, wherein said modified cytochrome C binds apoptosis protease activation factor-1 (Apaf-1) at least 1000 times less than wild type cytochrome C.

5. The fusion construct of claim 1, wherein said fluorescent protein is selected from the group consisting of Green Fluorescent Protein (GFP), Yellow Fluorescent Protein (YFP), Blue Fluorescent Protein (BFP), Cyan Fluorescent Protein (CFP), Red Fluorescent Protein (RFP), Enhanced Green Fluorescent Protein (EGFP) and Emerald.

6. The fusion construct of claim 1, wherein said fluorescent protein is Enhanced Green Fluorescent Protein or Emerald.

7. The fusion construct of claim 5, wherein said GFP comprises:
   i) an amino acid substitution at position F64L;
   ii) an amino acid substitution at position S175G; and
   iii) an amino acid substitution at position E222G.

8. The fusion construct of claim 1 selected from the group consisting of SEQ ID NO: 4 and SEQ ID NO: 6.

9. A nucleotide sequence encoding the fusion construct of claim 1.

10. A nucleotide sequence selected from the group consisting of SEQ ID NO: 3 and SEQ ID NO 5.

11. A nucleic acid construct comprising a suitable control region and the nucleotide sequence of claim 9, said sequence being under the control of said control region.

12. The nucleic acid construct of claim 11 being under the control of a promoter selected from the group consisting of native cytochrome C promoter, mammalian constitutive promoter, mammalian regulatory promoter, human ubiquitin C promoter, viral promoter, SV40 promoter, CMV promoter, yeast promoter, filamentous fungal promoter and bacterial promoter.

13. The nucleic acid construct of claim 12, wherein said viral promoter is the CMV or the SV40 promoter.

14. The nucleic acid construct of claim 12, wherein the promoter is the human ubiquitin C promoter.

15. A replicable vector comprising the nucleic acid construct of claim 11.

16. The replicable vector of claim 15, wherein said vector is a plasmid vector.

17. The replicable vector of claim 15, wherein the vector is a viral vector.

18. The replicable vector of claim 17, wherein said viral vector is selected from the group consisting of cytomegalovirus, Herpes simplex virus, Epstein-Barr virus, Simian virus 40, Bovine papillomavirus, Adeno-associated virus, Adenovirus, Vaccina virus and Baculovirus vector.

19. A host cell stably transformed with the nucleic acid construct of claim 11.

20. A host cell transiently transformed with the nucleic acid construct of claim 11.

21. The host cell of claim 19 selected from the group consisting of plant, insect, nematode, bird, fish and mammalian cell.

22. The host cell of claim 21, wherein said mammalian cell is a human cell.

23. The host cell of claim 22, wherein said human cell is selected from the group consisting of Hek, HeLa, U2OS and MCF-7.

24. The host cell of claim 23, wherein said Hek cell is Hek293.

25. The host cell of claim 19 capable of expressing the fusion protein of claim 1.

26. A method for detecting apoptosis in a living cell comprising the steps of:
   i) culturing a cell transformed to over-express the fusion construct of claim 1; and
   ii) determining the localisation of the fusion construct within the cell with time;
   wherein a change in localisation of the fusion construct within the cell is indicative of apoptosis.

27. The method of claim 26, wherein the localisation of said fusion construct is measured by its luminescence, fluorescence or radioactive properties.

28. The method of claim 26, wherein the localisation of the protein fusion is determined following fixation of the cells.

29. The method of claim 26, where the agent is a chemical, physical or biological agent.

* * * * *

SEQUENCE LISTING

```
<160> NUMBER OF SEQ ID NOS: 15

<210> SEQ ID NO 1
<211> LENGTH: 315
<212> TYPE: DNA
<213> ORGANISM: Homo sapiens

<400> SEQUENCE: 1
atgggtgatg ttgagaaagg caagaagatt tttattatga agtgttccca gtgccacacc      60
gttgaaaagg gaggcaagca caagactggg ccaaatctcc atggtctctt tgggcggaag     120
acaggtcagg cccctggata ctcttacaca gccgccaata agaacaaagg catcatctgg     180
ggagaggata cactgatgga gtatttggag aatcccaaga agtacatccc tggaacaaaa     240
```

```
atgatctttg tcggcattaa gaagaaggaa gaaagggcag acttaatagc ttatctcaaa     300
aaagctacta atgag                                                      315
```

<210> SEQ ID NO 2
<211> LENGTH: 105
<212> TYPE: PRT
<213> ORGANISM: Homo sapiens

<400> SEQUENCE: 2

```
Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Lys Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu
            100                 105
```

<210> SEQ ID NO 3
<211> LENGTH: 1044
<212> TYPE: DNA
<213> ORGANISM: Artificial Sequence
<220> FEATURE:
<223> OTHER INFORMATION: Synthetic oligonucleotide

<400> SEQUENCE: 3

```
atgagtaaag gagaagaact tttcactgga gttgtcccaa ttcttgttga attagatggt      60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactc tctcttatgg tgttcaatgc ttttcaagat acccagatca tatgaaacgg    240
catgactttt tcaagagtgc catgcccgaa ggttatgtac aggaaagaac tatatttttc    300
aaagatgacg ggaactacaa gacacgtgct gaagtcaagt ttgaaggtga tacccttgtt    360
aatagaatcg agttaaaagg tattgatttt aagaagatg gaaacattct tggacacaaa    420
ttggaataca actataactc acacaatgta tacatcatgg cagacaaaca aaagaatgga    480
atcaaagtta acttcaaaat tagacacaac attgaagatg gaggcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttggctttg taacagctgc tgggattaca catggcatgg atgaactata caaactcgag    720
aattcgacca tggtgatgt tgagaaaggc aagaagattt ttattatgaa gtgttcccag    780
tgccacaccg ttgaaaaggg aggcaagcac aagactgggc aaatctcca tggtctcttt    840 gggcggaaga caggtcaggc ccctggatac tcttacacag ccgccaataa gaacaaaggc    900
atcatctggg gagaggatac actgatggag tatttggaga atcccgccaa gtacatccct    960
ggaacaaaaa tgatctttgt cggcattaag aagaaggaag aaagggcaga cttaatagct   1020
tatctcaaaa aagctactaa tgag                                          1044
```

<210> SEQ ID NO 4
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 4

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Gly Phe Val
    210                 215                 220

Thr Ala Ala Gly Ile Thr His Gly Met Asp Glu Leu Tyr Lys Leu Glu
225                 230                 235                 240

Asn Ser Thr Met Gly Asp Val Glu Lys Gly Lys Lys Ile Phe Ile Met
                245                 250                 255

Lys Cys Ser Gln Cys His Thr Val Glu Lys Gly Gly Lys His Lys Thr
            260                 265                 270

Gly Pro Asn Leu His Gly Leu Phe Gly Arg Lys Thr Gly Gln Ala Pro
        275                 280                 285

Gly Tyr Ser Tyr Thr Ala Ala Asn Lys Asn Lys Gly Ile Ile Trp Gly
    290                 295                 300

Glu Asp Thr Leu Met Glu Tyr Leu Glu Asn Pro Ala Lys Tyr Ile Pro
305                 310                 315                 320

Gly Thr Lys Met Ile Phe Val Gly Ile Lys Lys Glu Glu Arg Ala
                325                 330                 335

Asp Leu Ile Ala Tyr Leu Lys Lys Ala Thr Asn Glu
            340                 345
```

<210> SEQ ID NO 5
<211> LENGTH: 1041
<212> TYPE: DNA

<213> ORGANISM: Artificial Sequence
<220> FEATURE:
<223> OTHER INFORMATION: Synthetic oligonucleotide

<400> SEQUENCE: 5

```
atgggtgatg ttgagaaagg caagaagatt tttattatga agtgttccca gtgccacacc      60
gttgaaaagg gaggcaagca aagactgggc caaatctcc atggtctctt tgggcggaag      120
acaggtcagg cccctggata ctcttacaca gccgccaata agaacaaagg catcatctgg     180
ggagaggata cactgatgga gtatttggag aatcccgcca agtacatccc tggaacaaaa     240
atgatctttg tcggcattaa gaagaaggaa gaaagggcag acttaatagc ttatctcaaa     300
aaagctacta atgagggtcg acccgggatg agtaaggag aagaactttt cactggagtt      360
gtcccaattc ttgttgaatt agatggtgat gttaatgggc acaaattttc tgtcagtgga     420
gagggtgaag gtgatgcaac atacggaaaa cttaccctta aatttatttg cactactgga     480
aaactacctg ttccatggcc aacacttgtc actactctct cttatggtgt tcaatgcttt     540
tcaagatacc cagatcatat gaaacggcat gactttttca agagtgccat gcccgaaggt     600
tatgtacagg aaagaactat attttttcaaa gatgacggga actacaagac acgtgctgaa    660
gtcaagtttg aaggtgatac ccttgttaat agaatcgagt taaaaggtat tgatttttaaa    720
gaagatggaa acattcttgg acacaaattg gaatacaact ataactcaca caatgtatac    780
atcatggcag acaaacaaaa gaatggaatc aaagttaact tcaaaattag acacaacatt    840
gaagatggag cgttcaact agcagaccat tatcaacaaa atactccaat tggcgatggc     900
cctgtccttt taccagacaa ccattacctg tccacacaat ctgcccttc gaaagatccc       960
aacgaaaaga gagaccacat ggtccttctt ggctttgtaa cagctgctgg gattacacat    1020
ggcatggatg aactatacaa a                                               1041
```

<210> SEQ ID NO 6
<211> LENGTH: 347
<212> TYPE: PRT
<213> ORGANISM: Artificial Sequence
<220> FEATURE:
<223> OTHER INFORMATION: Synthetic polypeptide

<400> SEQUENCE: 6

```
Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Ala Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu Gly Arg Pro Gly Met Ser Lys
            100                 105                 110

Gly Glu Glu Leu Phe Thr Gly Val Val Pro Ile Leu Val Glu Leu Asp
        115                 120                 125

Gly Asp Val Asn Gly His Lys Phe Ser Val Ser Gly Glu Gly Glu Gly
    130                 135                 140

Asp Ala Thr Tyr Gly Lys Leu Thr Leu Lys Phe Ile Cys Thr Thr Gly
```

```
            145                 150                 155                 160
Lys Leu Pro Val Pro Trp Pro Thr Leu Val Thr Thr Leu Ser Tyr Gly
                165                 170                 175
Val Gln Cys Phe Ser Arg Tyr Pro Asp His Met Lys Arg His Asp Phe
            180                 185                 190
Phe Lys Ser Ala Met Pro Glu Gly Tyr Val Gln Glu Arg Thr Ile Phe
        195                 200                 205
Phe Lys Asp Asp Gly Asn Tyr Lys Thr Arg Ala Glu Val Lys Phe Glu
    210                 215                 220
Gly Asp Thr Leu Val Asn Arg Ile Glu Leu Lys Gly Ile Asp Phe Lys
225                 230                 235                 240
Glu Asp Gly Asn Ile Leu Gly His Lys Leu Glu Tyr Asn Tyr Asn Ser
            245                 250                 255
His Asn Val Tyr Ile Met Ala Asp Lys Gln Lys Asn Gly Ile Lys Val
        260                 265                 270
Asn Phe Lys Ile Arg His Asn Ile Glu Asp Gly Gly Val Gln Leu Ala
    275                 280                 285
Asp His Tyr Gln Gln Asn Thr Pro Ile Gly Asp Gly Pro Val Leu Leu
    290                 295                 300
Pro Asp Asn His Tyr Leu Ser Thr Gln Ser Ala Leu Ser Lys Asp Pro
305                 310                 315                 320
Asn Glu Lys Arg Asp His Met Val Leu Leu Gly Phe Val Thr Ala Ala
            325                 330                 335
Gly Ile Thr His Gly Met Asp Glu Leu Tyr Lys
            340                 345

<210> SEQ ID NO 7
<211> LENGTH: 1044
<212> TYPE: DNA
<213> ORGANISM: Artificial Sequence
<220> FEATURE:
<223> OTHER INFORMATION: synthetic oligonucleotide

<400> SEQUENCE: 7
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactc tctcttatgg tgttcaatgc ttttcaagat acccagatca tatgaaacgg    240
catgactttt tcaagagtgc catgcccgaa ggttatgtac aggaaagaac tatatttttc    300
aaagatgacg ggaactacaa gacacgtgct gaagtcaagt ttgaaggtga taccttgtt    360 aatagaatcg agttaaaagg tattgatttt aagaagatg gaaacattct tggacacaaa    420
ttggaataca actataactc acacaatgta tacatcatgg cagacaaaca aaagaatgga    480
atcaaagtta acttcaaaat tagacacaac attgaagatg gaggcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttggctttg taacagctgc tgggattaca catggcatgg atgaactata caaactcgag    720
aattcgacca tgggtgatgt tgagaaaggc aagaagattt tattatgaa gtgttcccag    780 tgccacaccg ttgaaaaggg aggcaagcac aagactgggc aaatctcca tggtctcttt    840 gggcggaaga caggtcaggc ccctggatac tcttacacag ccgccaataa gaacaaaggc    900
atcatctggg gagaggatac actgatggag tatttggaga tcccaagaa gtacatccct    960
```

```
ggaacaaaaa tgatctttgt cggcattaag aagaaggaag aaagggcaga cttaatagct   1020
tatctcaaaa aagctactaa tgag                                          1044
```

<210> SEQ ID NO 8
<211> LENGTH: 348
<212> TYPE: PRT
<213> ORGANISM: Artificial Sequence
<220> FEATURE:
<223> OTHER INFORMATION: Synthetic polypeptide

<400> SEQUENCE: 8

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Gly Phe Val
    210                 215                 220

Thr Ala Ala Gly Ile Thr His Gly Met Asp Glu Leu Tyr Lys Leu Glu
225                 230                 235                 240

Asn Ser Thr Met Gly Asp Val Glu Lys Gly Lys Lys Ile Phe Ile Met
                245                 250                 255

Lys Cys Ser Gln Cys His Thr Val Glu Lys Gly Gly Lys His Lys Thr
            260                 265                 270

Gly Pro Asn Leu His Gly Leu Phe Gly Arg Lys Thr Gly Gln Ala Pro
        275                 280                 285

Gly Tyr Ser Tyr Thr Ala Ala Asn Lys Asn Lys Gly Ile Ile Trp Gly
    290                 295                 300

Glu Asp Thr Leu Met Glu Tyr Leu Glu Asn Pro Lys Lys Tyr Ile Pro
305                 310                 315                 320

Gly Thr Lys Met Ile Phe Val Gly Ile Lys Lys Lys Glu Glu Arg Ala
                325                 330                 335

Asp Leu Ile Ala Tyr Leu Lys Lys Ala Thr Asn Glu
            340                 345
```

<210> SEQ ID NO 9
<211> LENGTH: 1041
<212> TYPE: DNA
<213> ORGANISM: Artificial Sequence
<220> FEATURE:
<223> OTHER INFORMATION: Synthetic oligonucleotide

<400> SEQUENCE: 9

```
atgggtgatg ttgagaaagg caagaagatt tttattatga agtgttccca gtgccacacc    60
gttgaaaagg gaggcaagca aagactggg ccaaatctcc atggtctctt tgggcggaag    120
acaggtcagg cccctggata ctcttacaca gccgccaata agaacaaagg catcatctgg   180
ggagaggata cactgatgga gtatttggag aatcccaaga agtacatccc tggaacaaaa   240
atgatctttg tcggcattaa gaagaaggaa gaaagggcag acttaatagc ttatctcaaa   300
aaagctacta atgagggtcg acccgggatg agtaaggag aagaactttt cactggagtt    360
gtcccaattc ttgttgaatt agatggtgat gttaatgggc acaaattttc tgtcagtgga   420
gagggtgaag gtgatgcaac atacggaaaa cttacccta aatttatttg cactactgga    480
aaactacctg ttccatggcc aacacttgtc actactctct cttatggtgt tcaatgcttt   540
tcaagatacc cagatcatat gaaacggcat gactttttca agagtgccat gcccgaaggt   600
tatgtacagg aaagaactat attttttcaaa gatgacggga actacaagac acgtgctgaa   660
gtcaagtttg aaggtgatac ccttgttaat agaatcgagt taaaaggtat tgatttaaaa   720
gaagatggaa acattcttgg acacaaattg gaatacaact ataactcaca caatgtatac   780
atcatggcag acaaacaaaa gaatggaatc aaagttaact tcaaaattag acacaacatt   840
gaagatggag cgttcaact agcagaccat tatcaacaaa atactccaat tggcgatggc   900
cctgtccttt taccagacaa ccattacctg tccacacaat ctgccctttc gaaagatccc   960
aacgaaaaga gagaccacat ggtccttctt ggctttgtaa cagctgctgg gattacacat   1020
ggcatggatg aactatacaa a                                             1041
```

<210> SEQ ID NO 10
<211> LENGTH: 347
<212> TYPE: PRT
<213> ORGANISM: Artificial Sequence
<220> FEATURE:
<223> OTHER INFORMATION: Synthetic polypeptide

<400> SEQUENCE: 10

Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Lys Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu Gly Arg Pro Gly Met Ser Lys
            100                 105                 110

Gly Glu Glu Leu Phe Thr Gly Val Val Pro Ile Leu Val Glu Leu Asp
        115                 120                 125

```
Gly Asp Val Asn Gly His Lys Phe Ser Val Ser Gly Glu Gly Glu Gly
        130                 135                 140

Asp Ala Thr Tyr Gly Lys Leu Thr Leu Lys Phe Ile Cys Thr Thr Gly
145                 150                 155                 160

Lys Leu Pro Val Pro Trp Pro Thr Leu Val Thr Thr Leu Ser Tyr Gly
                165                 170                 175

Val Gln Cys Phe Ser Arg Tyr Pro Asp His Met Lys Arg His Asp Phe
            180                 185                 190

Phe Lys Ser Ala Met Pro Glu Gly Tyr Val Gln Glu Arg Thr Ile Phe
        195                 200                 205

Phe Lys Asp Asp Gly Asn Tyr Lys Thr Arg Ala Glu Val Lys Phe Glu
210                 215                 220

Gly Asp Thr Leu Val Asn Arg Ile Glu Leu Lys Gly Ile Asp Phe Lys
225                 230                 235                 240

Glu Asp Gly Asn Ile Leu Gly His Lys Leu Glu Tyr Asn Tyr Asn Ser
                245                 250                 255

His Asn Val Tyr Ile Met Ala Asp Lys Gln Lys Asn Gly Ile Lys Val
            260                 265                 270

Asn Phe Lys Ile Arg His Asn Ile Glu Asp Gly Gly Val Gln Leu Ala
        275                 280                 285

Asp His Tyr Gln Gln Asn Thr Pro Ile Gly Asp Gly Pro Val Leu Leu
290                 295                 300

Pro Asp Asn His Tyr Leu Ser Thr Gln Ser Ala Leu Ser Lys Asp Pro
305                 310                 315                 320

Asn Glu Lys Arg Asp His Met Val Leu Leu Gly Phe Val Thr Ala Ala
                325                 330                 335

Gly Ile Thr His Gly Met Asp Glu Leu Tyr Lys
            340                 345

<210> SEQ ID NO 11
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 11
gttgaattcg accatgggtg atgttgagaa aggc                              34

<210> SEQ ID NO 12
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 12
gttgttgtcg accttactca ttagtagctt ttttgag                           37

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 13
gttgttgtcg accctcatta gtagcttttt tgag                              34

<210> SEQ ID NO 14
```

-continued

```
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 14
ggagtatttg gagaatcccg ccaagtacat ccctggaaca a                         41

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 15
ttgttccagg gatgtacttg gcgggattct ccaaatactc c                         41
```